(12) United States Patent
Rich

(10) Patent No.: US 7,077,064 B1
(45) Date of Patent: Jul. 18, 2006

(54) METHODS FOR MEASUREMENT AND CONTROL OF INK CONCENTRATION AND FILM THICKNESS

(75) Inventor: Danny Rich, Trenton, NJ (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 11/110,318

(22) Filed: Apr. 19, 2005

(51) Int. Cl.
*B41F 1/54* (2006.01)
*G01J 3/46* (2006.01)
*G01N 21/25* (2006.01)

(52) U.S. Cl. .................. 101/484; 356/402; 356/407

(58) Field of Classification Search ........... 101/484, 101/213, 483, 356, 349.1, 147, 216; 356/407, 356/402; 348/93, 187; 382/199, 122; 358/475
See application file for complete search history.

(56) References Cited

U.S. PATENT DOCUMENTS

| | | | | |
|---|---|---|---|---|
| 4,289,405 A | | 9/1981 | Tobias | 356/407 |
| 4,494,875 A | * | 1/1985 | Schramm et al. | 356/402 |
| 4,671,661 A | * | 6/1987 | Ott | 356/402 |
| 4,690,564 A | * | 9/1987 | Morgenstern et al. | 356/445 |
| 4,971,446 A | * | 11/1990 | Kurata | 356/402 |
| 5,122,977 A | * | 6/1992 | Pfeiffer | 101/211 |
| 5,163,012 A | | 11/1992 | Wuhrl et al. | 382/122 |
| 5,526,285 A | * | 6/1996 | Campo et al. | 356/405 |
| 5,724,259 A | | 3/1998 | Seymour et al. | 382/199 |
| 5,767,980 A | | 6/1998 | Wang et al. | 358/475 |
| 5,774,225 A | | 6/1998 | Goldstein et al. | 356/402 |
| 5,821,993 A | | 10/1998 | Robinson | 348/187 |
| 6,003,967 A | * | 12/1999 | Mazaki | 347/19 |
| 6,151,064 A | | 11/2000 | Connolly et al. | 348/93 |
| 6,832,550 B1 | * | 12/2004 | Martin et al. | 101/349.1 |
| 6,901,861 B1 | * | 6/2005 | Adachi et al. | 101/483 |
| 7,000,544 B1 | * | 2/2006 | Riepenhoff | 101/484 |

FOREIGN PATENT DOCUMENTS

JP          363118602 A  *  5/1988

OTHER PUBLICATIONS

Stocka, D., "Are intervals of 20nm sufficient for industrial color measurement?", *COL-OUR 73*, Adam Hilger, London, 453-456, (1973).
Billmeyer, F.W., Beasley, J. K., Sheldon, J. A., "Formulation of transparent colors with a digital computer", *Journal of the Optical Society of America*, 50, 70-72, (1960).

* cited by examiner

*Primary Examiner*—Andrew H. Hirshfeld
*Assistant Examiner*—Wasseem H. Hamdan
(74) *Attorney, Agent, or Firm*—Kramer Levin Naftalis & Frankel LLP

(57) ABSTRACT

A process is disclosed to measure or monitor ink concentration or ink thickness of an ink film as printed on a printing press, which consists of measuring light reflected from the ink film and the ink substrate.

4 Claims, 1 Drawing Sheet

METHODS FOR MEASUREMENT AND CONTROL OF INK CONCENTRATION AND FILM THICKNESS

FIELD OF THE INVENTION

The invention relates to predicting or determining ink concentration and/or ink thickness on an on-line printing process.

BACKGROUND OF THE INVENTION

Online inspection of printed materials is realized in the prior art through the use of either a densitometer attached to the printing press that reads small area of ink along the edge of the substrate, known as test targets or through the use of an electronic color video or color digital camera that reads either the test targets or specified areas within the printed image. Disclosures of such prior art are found in U.S. Pat. Nos. 4,289,405; 5,163,012; and 5,774,225.

In those methods that utilize a color video camera, the camera is used as a light sensor with three wide-band light detectors, commonly referred to as Red, Green or Blue (RGB) with spectral sensitivities that peak in the "blue", "green" or "red" regions of the visible spectrum. The light sensor integrates or sums all of the light rays with wavelengths within its passband. The camera sensors are then used to approximate the responses of a Standard ISO Status Density, as defined in ISO 5/3. It is important to note that the spectral response of the three camera sensors only approximate the ISO Status Density spectral curves.

The densitometer or the camera measures "substrate relative" density. That is, the camera is first pointed to the unprinted substrate and the light projected onto the substrate. The projected light that is reflected from the substrate is collected by camera in each of its three sensors. Typical RGB camera signals are binary coded values with a range of 0 to 255 (8 bits). The camera is adjusted so that a perfect white object will read RGB values (255, 255, 255). The values are normalized so that the perfect white will have relative values of (1.0, 1.0, 1.0) as is disclosed in U.S. Pat. Nos. 5,724,259 and 5,767,980. The normalized values of the sensors are converted into density by computing the negative of the logarithm of the sensor value. Next, a printed area is move into the field of view of the camera and the light projected onto that area. The camera captures the light reflected from the printed area, comprised of the ink and the substrate. The camera readings are again converted to density. The previously computed substrate density is then subtracted from the ink-on-substrate density to leave only the density of the ink. The density of the ink is assumed to be proportional to the thickness of the ink layer.

Because of the differences between the camera sensors and an ISO Status Densitometer, it is not possible to simultaneously obtain colorant concentration and ink film thickness. On a commercial offset press the only parameter that is available to the pressman to control is the weight of ink applied to the substrate which modulates the ink film thickness. Accordingly, there is a need in the printing industry to have a press inspection system that measures and tacks the color and the concentration of the inks as they are being printed.

SUMMARY OF THE INVENTION

The present invention provides a method of measuring printed ink concentration on an opaque substrate on-line comprising:

(a) projecting a light over the ink printed on the substrate measuring light reflectance as a camera response R, G or B, wherein R is the camera response for a red sensor, G is the camera response for a green sensor and B is the camera response for a Blue sensor;

(b) Substituting the camera response R, G or B for reflectance ($\rho$) of the printed ink over the opaque substrate in order to calculate the ratio of absorption to scattering (K/S) as indicated in the following formula $$\frac{K}{S} = \frac{(1-\rho)^2}{2\rho}; \text{ and}$$

(c) calculating printed ink concentration (c) based on the following formula:

$$\frac{K}{S} = \frac{k}{s} \times c \times t$$

wherein (K/S) is as calculated in step (b), (k/s) is the relative (relative to the scattering of the substrate) unit absorption coefficient, a predetermined measurement of the pre-printed ink per unit concentration per unit thickness and (t) is the thickness of the printed ink either predetermined prior to or measured after printing.

The present invention also provides a method of measuring printed ink thickness on a substrate on-line comprising:

(a) projecting a light over the ink printed on the substrate measuring light reflectance as a camera response R, G or B, wherein R is the camera response for a red sensor, G is the camera response for a green sensor and B is the camera response for a Blue sensor;

(b) Substituting the camera response R, G or B for reflectance ($\rho$) of the printed ink over the opaque substrate in order to calculate the ratio of absorption to scattering (K/S) as indicated in the following formula $$\frac{K}{S} = \frac{(1-\rho)^2}{2\rho}; \text{ and}$$

(c) calculating printed ink thickness (t) based on the following formula:

$$\frac{K}{S} = \frac{k}{s} \times c \times t$$

wherein (K/S) is as calculated in step (b), (k/s) is the relative (relative to the scattering of the substrate) unit absorption coefficient, a predetermined measurement of the pre-printed ink per unit concentration per unit thickness and c is the concentration of the printed ink either predetermined prior to or measured after printing.

Other objects and advantages of the present invention will become apparent from the following description and appended claims.

DETAILED DESCRIPTION OF THE INVENTION

Figure 1:
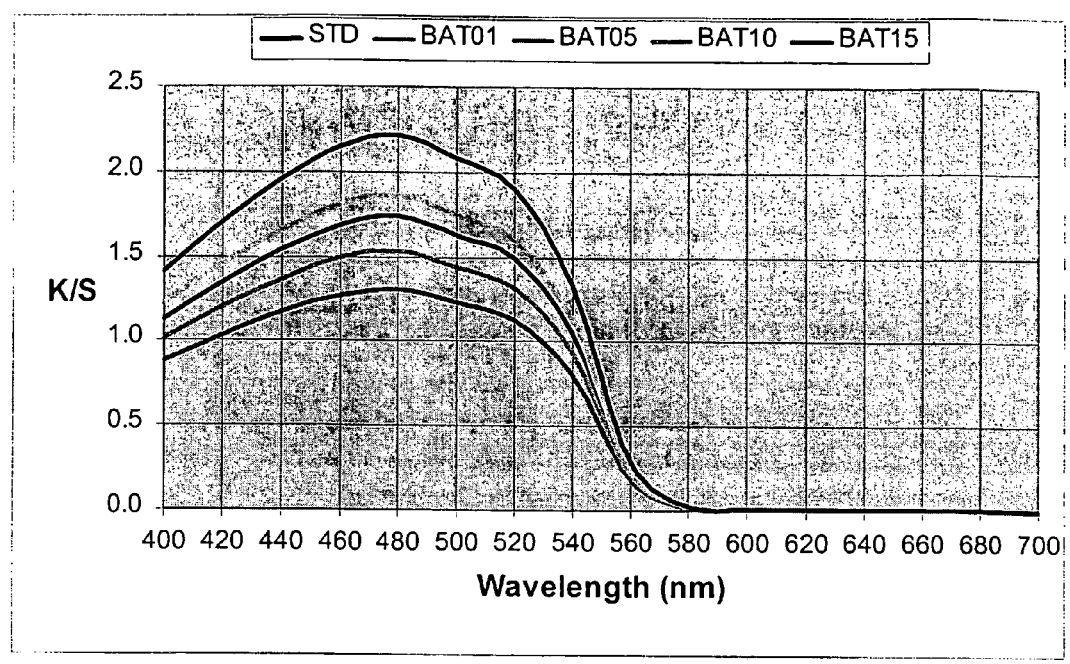
FIG. 1 shows plots of the spectral K/S for a series of inks with varying amounts of pigments in the ink.

A method has been discovered to measuring the reflectance of an ink film as printed on a printing press, and during the operation of that press with the intent of monitoring the ink concentration and the ink film thickness.

Accordingly, the camera sensor in the present invention is used as an absolute reflectometer. The camera is not standardized to the substrate but to an absolute white standard, as disclosed in U.S. Pat. Nos. 5,821,993 and 6,151,064. The measurements of the substrate, the ink on the substrate are all made on the same basis as readings made off-line on a spectrophotometer or spectrocolorimeter. Knowing the spectral response of the camera will allow the offline instrument to approximate the camera measurements on the off-line spectral instrument and provide absolute data to the camera about the color, film thickness and concentration dependence of the ink.

When the press is operating, the camera may be used to capture the color of the press sheets during startup and compare them to the standard values computed off-line. This greatly reduces the print "make-ready" time for the printer. Getting acceptable prints sooner results in lower waste amounts and in better utilization of the printing machinery.

Additionally the camera may be used to monitor the color of the printing through out the run by comparing the current printed image to the laboratory colors or to the colors in the first acceptable image. If the color begins to drift, the data supplied by the camera may be used to adjust either the ink film thickness (also known as the film weight) or the concentration of base color in the ink well using the process described below.

In offset lithography, the inks are very thick pastes, loaded with as much pigment as modern chemical engineering can allow. The paste is mixed with water, either from a press fountain or at the ink factory in the form of pre-emulsified ink. The only operational controls on the press, known as "keys" control the amount of ink transferred from the roller train to the plate and from the plate to the blanket and from the blanket to the substrate. Since the ink does not evaporate, the weight of film on the substrate can be determined indirectly by weighing the rollers before and after printing. The difference in weight represents the amount of ink transferred. The film weight or thickness is historically controlled, offline by status densitometry.

In direct gravure printing or flexographic printing, the inks are thin liquids and the amount of ink transferred is controlled by the size and shape of the impressions in the gravure cylinder or anilox cylinder. The film thickness is quite difficult or nearly impossible to assess, even offline. Because the inks are thin liquids, held in simple wells, it is possible to adjust the amount of base ink relative to the printing solvent and thus adjust the concentration of the pigment in the ink transferred to the substrate.

One well known method for computing the optical properties of a thin, transparent, pigmented coating in the laboratory uses the model of turbid media developed by Kubelka and Munk in the 1940s. In this model the coating is assumed to be transparent and absorbing of light and the substrate is assumed to be opaque and scattering of light. The ratio of absorption (K) to scattering (S) is derived from the reflectance ($\rho$) of the transparent coatings over the opaque substrate as shown in equation 1.

$$\frac{K}{S} = \frac{(1-\rho)^2}{2\rho} \quad (1)$$

This derivation assumed that the light was taken in small increments of energy or wavelength bands, such as found in monochromatic light. In fact, it has been reported that narrow bands of wavelength are not needed for color control (Billmeyer, F. W., Beasley, J. K., Sheldon, J. A., "Formulation of transparent colors with a digital computer", *Journal of the Optical Society of America*, 50, 70–72, (1960); and Strocka, D., "Are intervals of 20 nm sufficient for industrial color measurement?", *COL-OUR* 73, Adam Hilger, London, 453–456, (1973)). In the application of this model to color formulation in the laboratory, it has been assumed that the ratio of absorption to scattering (K/S) is modulated by both the concentration (c) of the absorbing species and the thickness (t) of the coating such that the total K/S is proportional to a value, k/s which is the relative (relative to the scattering of the substrate) unit absorption coefficient, a predetermined measurement of the pre-printed ink per unit concentration per unit thickness as shown in equation 2.

$$\frac{K}{S} = \frac{k}{s} \times c \times t \quad (2)$$

Using this formalism, it is possible to substitute a camera response (R, G, or B) or a CIE calorimetric response (X, Y, or Z), obtained by linear transformation from RGB for the value of $\rho$ in equation 1 thus yielding an equation that can be used to control either the film thickness (t) or the concentration (c) using readings captured by the camera on-line over a printing press.

$$\left[\frac{K}{S}\right]_R = \frac{(1-R)^2}{2R}$$
$$\left[\frac{K}{S}\right]_G = \frac{(1-G)^2}{2G} \quad (3)$$
$$\left[\frac{K}{S}\right]_B = \frac{(1-B)^2}{2B}$$

In Table 1, an abridged table of camera spectral response functions for a typical RGB video camera is given. This data is illustrated in FIG. 1. In Tables 2a and 2b, are a series of spectral reflectance curves measured in a laboratory with a spectrocolorimeter for a range of colorant concentrations and for the same ink and concentration in three labs resulting in a series of differing film weights. In Tables 3a and 3b, the camera responses for the spectral data in Tables 2a and 2b are shown. These are simulated by numerical convolution of the camera response functions with the spectral reflectance curves. Such a simulation is documented in international standards such as ISO 5/3 (ISO 5/3 "Photography—Density measurements—Part 3 Spectral Conditions", International Organization for Standardization, Case Postale 56, CH-1211, Genève 20, Switzerland (1995)) and ASTM E-308 (ASTM E 308, "Computing the Colors of Objects by Using the CIE System", ASTM International, West Conshohocken, Pa., (2001)).

EXAMPLE 1

Measuring and Correcting Ink Film Weight

Equation (1) was applied to the reflectance data in Tables 2a and 2b and equation (3) to camera data in Tables 3a and 3b. Table 4 shows the Kubelka-Munk values and the estimates of the relative film weights of the ink films computed from the spectral data and the same information computed from the camera response values converted to Kubelka-Munk values. The relative film weight is computed as the ratio of the Kubelka-Munk (K/S) values for the various labs to those of the first lab. The results show that the relative thickness values computed from the CIE values and from the camera values are approximately equal, at least to within the noise of the readings.

EXAMPLE 2

Measuring and Correcting Ink Base Concentration

Equation (1) was applied to the reflectance data in Tables 2a and 2b and equation (3) to camera data in Tables 3a and 3b. Table 5 shows the Kubelka-Munk values and the estimates of the relative concentrations (strength) of the ink films computed from the spectral data and the same information computed from the camera response values converted to Kubelka-Munk values. The strength is computed as the ratio of the Kubelka-Munk (K/S) values for the various ink batches to those of the standard ink. The results show that the relative concentration (strength) computed from the CIE values and from the camera values are approximately equal, at least to within the noise of the readings.

TABLE 1

Spectral response of a typical RGB video camera

| Wavelength | Red sensor | Green sensor | Blue sensor |
|---|---|---|---|
| 400 | 0.000177 | 0.001082 | 0.03663 |
| 420 | 0.000950 | 0.001933 | 0.18529 |
| 440 | 0.001119 | 0.002410 | 0.27042 |
| 460 | 0.001114 | 0.002435 | 0.29388 |
| 480 | 0.000761 | 0.004262 | 0.19861 |
| 500 | 0.000711 | 0.162198 | 0.00383 |
| 520 | 0.001122 | 0.286955 | 0.00106 |
| 540 | 0.001339 | 0.283162 | 0.00101 |
| 560 | 0.041264 | 0.216318 | 0.00117 |
| 580 | 0.309783 | 0.032398 | 0.00288 |
| 600 | 0.298412 | 0.003166 | 0.00261 |
| 620 | 0.191670 | 0.001921 | 0.00166 |
| 640 | 0.098084 | 0.000981 | 0.00081 |
| 660 | 0.040003 | 0.000462 | 0.00028 |
| 680 | 0.012703 | 0.000188 | 0.00000 |
| 700 | 0.000788 | 0.000127 | −0.00015 |
| SUM | 1.000001 | 0.999999 | 1.000000 |

TABLE 2a

Spectral reflectance factors and CIE coordinates of a series of prints with differing ink concentrations

| Wavelength | STD | BAT01 | BAT05 | BAT10 | BAT15 |
|---|---|---|---|---|---|
| 400 | 24.93 | 28.84 | 26.62 | 23.76 | 21.71 |
| 420 | 22.37 | 26.30 | 24.03 | 21.28 | 19.17 |
| 440 | 20.47 | 24.38 | 22.15 | 19.53 | 17.38 |
| 460 | 19.30 | 23.19 | 20.94 | 18.4 | 16.29 |
| 480 | 18.91 | 22.81 | 20.54 | 18.03 | 15.92 |
| 500 | 19.75 | 23.71 | 21.43 | 18.83 | 16.67 |
| 520 | 20.93 | 24.98 | 22.66 | 19.99 | 17.76 |
| 540 | 25.97 | 30.22 | 27.85 | 24.98 | 22.51 |
| 560 | 50.85 | 54.40 | 52.55 | 49.97 | 47.42 |
| 580 | 81.00 | 81.65 | 81.28 | 80.83 | 79.86 |
| 600 | 87.23 | 87.05 | 86.99 | 87.3 | 87.11 |
| 620 | 87.85 | 87.57 | 87.66 | 88.1 | 87.89 |
| 640 | 87.72 | 87.48 | 87.56 | 88.05 | 87.76 |
| 660 | 88.81 | 88.61 | 88.63 | 89.09 | 88.8 |
| 680 | 90.55 | 90.34 | 90.32 | 90.74 | 90.42 |
| 700 | 92.89 | 92.66 | 92.67 | 93.03 | 92.73 |
| X | 59.73 | 61.26 | 60.36 | 59.4 | 58.24 |
| Y | 48.38 | 51.04 | 49.53 | 47.78 | 46.04 |
| Z | 21.64 | 25.83 | 23.41 | 20.63 | 18.34 |

TABLE 2b

Spectral reflectance factors and CIE coordinates of a series of prints with differing ink film weights

| Wavelength | Lab 1 | Lab 2 | Lab 3 |
|---|---|---|---|
| 400 | 23.87 | 24.03 | 22.40 |
| 420 | 23.58 | 23.72 | 22.03 |
| 440 | 25.56 | 25.71 | 23.95 |
| 460 | 23.62 | 23.82 | 21.96 |
| 480 | 17.38 | 17.63 | 15.87 |
| 500 | 12.32 | 12.58 | 11.09 |
| 520 | 8.45 | 8.63 | 7.58 |
| 540 | 7.61 | 7.70 | 6.90 |
| 560 | 6.97 | 6.90 | 6.44 |
| 580 | 11.29 | 11.02 | 10.58 |
| 600 | 46.27 | 46.23 | 45.14 |
| 620 | 77.77 | 77.92 | 77.54 |
| 640 | 84.13 | 84.17 | 84.02 |
| 660 | 86.66 | 86.69 | 86.62 |
| 680 | 89.10 | 89.05 | 88.99 |
| 700 | 90.37 | 90.36 | 90.26 |
| X | 33.31 | 33.32 | 32.54 |
| Y | 20.65 | 20.69 | 19.83 |
| Z | 24.41 | 24.61 | 22.72 |

TABLE 3a

Camera responses for the of a series of prints with differing ink concentrations

| Sensor Color | Std | Bat01 | Bat05 | Bat10 | Bat15 |
|---|---|---|---|---|---|
| R | 83.60 | 83.83 | 83.63 | 83.62 | 83.05 |
| G | 31.04 | 34.88 | 32.73 | 30.13 | 27.83 |
| B | 20.89 | 24.77 | 22.54 | 19.95 | 17.84 |

TABLE 3b

Camera responses for the of a series of prints with differing film weights

| Sensor Color | Lab - 1 | Lab - 2 | Lab - 3 |
|---|---|---|---|
| R | 45.54 | 45.48 | 44.90 |
| G | 9.16 | 9.26 | 8.35 |
| B | 22.98 | 23.16 | 21.41 |

TABLE 4

Kubelka-Munk values and relative film weights for the data of Tables 2b and 3b

| Wavelength | Lab - 1 | Lab - 2 | Lab - 3 |
|---|---|---|---|
| 400 | 1.2140 | 1.2009 | 1.3441 |
| 420 | 1.2383 | 1.2265 | 1.3798 |
| 440 | 1.0840 | 1.0733 | 1.2074 |
| 460 | 1.2350 | 1.2182 | 1.3867 |
| 480 | 1.9638 | 1.9242 | 2.2299 |
| 500 | 3.1200 | 3.0375 | 3.5640 |
| 520 | 4.9594 | 4.8369 | 5.6342 |
| 540 | 5.6084 | 5.5320 | 6.2809 |
| 560 | 6.2085 | 6.2809 | 6.7962 |
| 580 | 3.4851 | 3.5923 | 3.7788 |
| 600 | 0.3120 | 0.3127 | 0.3334 |
| 620 | 0.0318 | 0.0313 | 0.0325 |
| 640 | 0.0150 | 0.0149 | 0.0152 |
| 660 | 0.0103 | 0.0102 | 0.0103 |
| 680 | 0.0067 | 0.0067 | 0.0068 |
| 700 | 0.0051 | 0.0051 | 0.0053 |
| X | 0.6676 | 0.6674 | 0.6993 |
| Y | 1.5247 | 1.5201 | 1.6200 |
| Z | 1.1703 | 1.1549 | 1.3144 |
| Film Thickness | 1.000 | 0.987 | 1.123 |
| R | 0.3256 | 0.3268 | 0.3381 |
| G | 4.5027 | 4.4454 | 5.0285 |
| B | 1.2905 | 1.2744 | 1.4429 |
| Filmy Thickness | 1.000 | 0.988 | 1.118 |

TABLE 5

Kubelka-Munk values and strengths for the data of Tables 2b and 3b

| Wavelength | STD | BAT01 | BAT05 | BAT10 | BAT15 |
|---|---|---|---|---|---|
| 400 | 1.130266 | 0.877903 | 1.011387 | 1.223177 | 1.411636 |
| 420 | 1.346986 | 1.032641 | 1.200882 | 1.456024 | 1.704092 |
| 440 | 1.544949 | 1.172761 | 1.368086 | 1.657814 | 1.96377 |
| 460 | 1.687174 | 1.272052 | 1.492475 | 1.809391 | 2.150818 |
| 480 | 1.738654 | 1.306071 | 1.536975 | 1.863306 | 2.220304 |
| 500 | 1.630396 | 1.227365 | 1.440328 | 1.749487 | 2.08275 |
| 520 | 1.493565 | 1.126501 | 1.319831 | 1.601201 | 1.904115 |
| 540 | 1.055148 | 0.805633 | 0.934582 | 1.126501 | 1.333785 |
| 560 | 0.237534 | 0.191118 | 0.214225 | 0.25045 | 0.291507 |
| 580 | 0.022284 | 0.02062 | 0.021557 | 0.022732 | 0.025396 |
| 600 | 0.009347 | 0.009633 | 0.009729 | 0.009238 | 0.009537 |
| 620 | 0.008402 | 0.008822 | 0.008686 | 0.008037 | 0.008343 |
| 640 | 0.008595 | 0.008959 | 0.008837 | 0.008109 | 0.008536 |
| 660 | 0.00705 | 0.00732 | 0.007293 | 0.00668 | 0.007063 |
| 680 | 0.004931 | 0.005165 | 0.005187 | 0.004725 | 0.005075 |
| 700 | 0.002721 | 0.002907 | 0.002819 | 0.002611 | 0.00285 |
| X | 0.13575 | 0.122493 | 0.130163 | 0.138751 | 0.149716 |
| Y | 0.275385 | 0.234824 | 0.257139 | 0.285363 | 0.316212 |
| Z | 1.418736 | 1.064884 | 1.252889 | 1.526805 | 1.817981 |
| Strength | 100.00% | 76.29% | 88.31% | 107.62% | 128.14% |
| R | 0.016094 | 0.015592 | 0.016018 | 0.016054 | 0.017292 |
| G | 0.766252 | 0.607962 | 0.691224 | 0.810144 | 0.935785 |
| B | 1.497542 | 1.142509 | 1.331444 | 1.60611 | 1.891502 |
| Strength | 100.00% | 76.29% | 88.91% | 107.25% | 126.31% |

The invention has been described in terms preferred embodiments thereof, but is more broadly applicable as will be understood by those skilled in the art. The scope of the invention is only limited by the following claims.

What is claimed is:

1. A method of measuring printed ink concentration on an opaque substrate on-line comprising:
    (a) projecting a light over the ink printed on the substrate measuring light reflectance as a camera response R, G or B, wherein R is the camera response for a red sensor, G is the camera response for a green sensor and B is the camera response for a Blue sensor;
    (b) Substituting the camera response R, G or B for reflectance (ρ) of the printed ink over the opaque substrate in order to calculate the ratio of absorption to scattering (K/S) as indicated in the following formula $$\frac{K}{S} = \frac{(1-\rho)^2}{2\rho}; \text{ and}$$

(c) calculating printed ink concentration (c) based on the following formula:

$$\frac{K}{S} = \frac{k}{s} \times c \times t$$

wherein (K/S) is as calculated in step (b), (k/s) is the relative (relative to the scattering of the substrate) unit absorption coefficient, a predetermined measurement of the pre-printed ink per unit concentration per unit thickness and (t) is the thickness of the printed ink either predetermined prior to or measured after printing.

2. The method of claim 1, wherein a xenon flash lamp is the source of the light.

3. A method of measuring printed ink thickness on a substrate on-line comprising:
    (a) projecting a light over the ink printed on the substrate measuring light reflectance as a camera response R, G or B, wherein R is the camera response for a red sensor, G is the camera response for a green sensor and B is the camera response for a Blue sensor;
    (b) Substituting the camera response R, G or B for reflectance (ρ) of the printed ink over the opaque substrate in order to calculate the ratio of absorption to scattering (K/S) as indicated in the following formula $$\frac{K}{S} = \frac{(1-\rho)^2}{2\rho}; \text{ and}$$

(c) calculating printed ink thickness (t) based on the following formula:

$$\frac{K}{S} = \frac{k}{s} \times c \times t$$

wherein (K/S) is as calculated in step (b), (k/s) is the relative (relative to the scattering of the substrate) unit absorption coefficient, a predetermined measurement of the pre-printed ink per unit concentration per unit thickness and (c) is the concentration of the printed ink either predetermined prior to or measured after printing.

4. The method of claim 3, wherein a xenon flash lamp is the source of the light.

* * * * *